Figure 1:
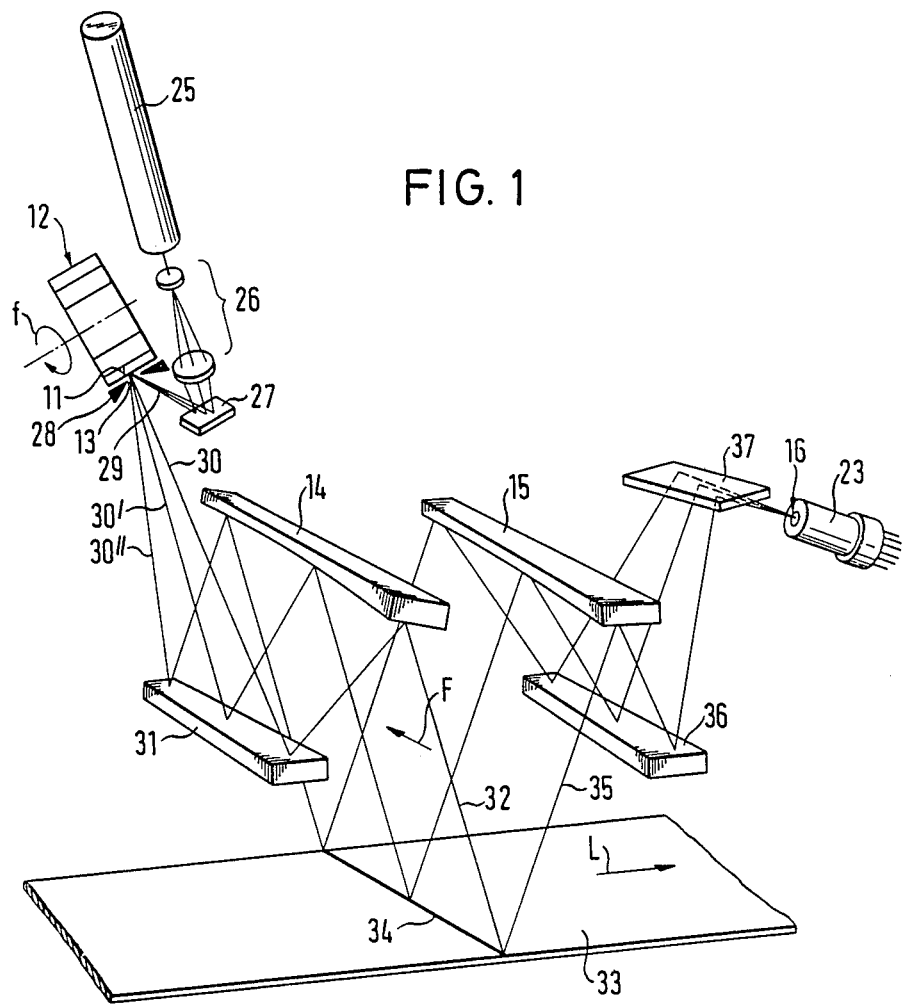

United States Patent [19]
Weber

[11] Patent Number: 4,866,288
[45] Date of Patent: Sep. 12, 1989

[54] APPARATUS FOR OPTICALLY SCANNING A WEB OF MATERIAL

[75] Inventor: Klaus Weber, Königsbronn, Fed. Rep. of Germany

[73] Assignee: Erwin Sick GmbH Optik-Elektronik, Waldkirch, Fed. Rep. of Germany

[21] Appl. No.: 897,002

[22] Filed: Aug. 15, 1986

[30] Foreign Application Priority Data

Sep. 24, 1985 [DE] Fed. Rep. of Germany ....... 3534018

[51] Int. Cl.⁴ ............................................. G01N 21/88
[52] U.S. Cl. ..................................... 250/572; 356/431
[58] Field of Search ............... 250/236, 234, 235, 562, 250/563, 559, 571, 572; 350/6.7, 6.8, 6.9; 356/430, 431

[56] References Cited

U.S. PATENT DOCUMENTS 3,854,587 12/1974 McLoughlin et al. ............. 250/562
4,118,127 10/1978 Klein et al. ......................... 250/563
4,409,477 10/1983 Carl ..................................... 250/236

Primary Examiner—David C. Nelms
Assistant Examiner—William L. Oen
Attorney, Agent, or Firm—Townsend and Townsend

[57] ABSTRACT

The sharply bounded entry pupil (13) of an optical web monitoring apparatus is imaged by the system after passage through or reflection at the material web onto a dark field stop (16). This stop is provided at its periphery with light receiving surfaces having a relatively small area relative to the extent of the dark field stop (16). These light receiving surfaces conduct the received light to a photoconverter arrangement which is connected to an electronic processing circuit. In this way material faults are detected which bring about only small angular deviations of the scanning beam. In order to detect faults with greater light scattering a multiplier (23) is additionally mounted behind this receiver arrangement and receives light deflected beyond the light receiving surfaces.

13 Claims, 4 Drawing Sheets

APPARATUS FOR OPTICALLY SCANNING A WEB OF MATERIAL

The invention relates to an optical web monitoring apparatus which, by means of a deflecting device and image forming optical elements, generates a point of light which cyclically scans the material web transverse to its longitudinal direction and concentrates light deflected or scattered on passage through the material, or on reflection at the material, onto a photo-receiver device.

In such optical web monitoring apparatuses it is already known to operate on the receiving side in the so-called dark field. This may, for example, be done to keep the non-scattered light reflected at specularly reflecting metal surfaces away from the photoreceivers at the receiver-side. In this way light beams which pass by the dark field stop as a result of faults give rise to a particularly pronounced fault signal.

It is also known to arrange a surface matrix consisting of numerous photoreceivers at the position on the receiver side where the reflecting surface of the mirror wheel is imaged via the specularly reflecting web surface. This makes it possible, through the attached electronic processing circuit to detect the scattering of the individual light beams which has taken place at the web. Numerous faults can be distinguished in accordance with their character through the determination of the scattering indicatrix.

While it is not possible, with arrangements which operate with a dark field stop, to differentiate between larger and smaller angles of scattering, the photoreceiver matrix lacks adequate sensitivity with regard to the large angles of scattering at which the light intensity is frequently already relatively weak.

The object of the invention is thus to provide an optical web monitoring apparatus of the initially named kind by means of which the light beams which have only been deflected to a small degree by the scanned material web, and which are thus still relatively intense, can be detected in simple manner, with the light beams which have been scattered to a greater degree and which are generally less intense being capable of being detected independently.

In order to satisfy this object the present invention proposes an arrangement of the initially named kind which is characterised in that a sharply bounded, preferably circular or rectangular bead of light is generated on the deflecting device, or a correspondingly shaped physical diaphragm is provided, which is imaged, through the optical scanning and receiving system, onto a complementary dark field stop, which is preferably slightly larger than the image of the light bead and which is provided along its periphery with light receiving surfaces, which are of small area relative to the extent of the dark field stop and which conduct the received light onto the photoconverter arrangement, which is connected to an electronic processing circuit.

The prerequisite for the detection of a very small scattering angle is that a light bead with very sharply defined contours, preferably a circular or rectangular light bead, is present in the entry pupil of the optically scanning device, i.e. for example on the reflecting mirror surface of the mirror wheel. This light bead can be generated either by the arrangement of a correspondingly shaped diaphragm directly at or on the mirror surface, or by imaging such a diaphragm onto the reflecting mirror surface. The mirror surface, or the sharply bounded light bead present thereon, is then for example exactly imaged onto the dark field stop on the receiver side. This can be done using the strip-like concave mirror or mirrors frequently used in web monitoring devices.

For fault-free specular reflection none of the light receiving surfaces are illuminated by scattered light so that no fault signal appears. If however streaks, bubbles, lenses or so-called fish-eyes occur in the foils, flat glass or similar smooth materials in transmission and/or reflexion then a small deflection of the reflected or transmitted light occurs which leads to the relevant light falling at the edge of the dark field stop onto one of the light receiving surfaces. This can be brought to an electrical indication by the subsequent photoconverter arrangement.

In a telecentric arrangement of transmitting and receiving concave mirrors the dark field stop with the light receiving surfaces arranged around it is located in the focal plane of the strip-like receiver-side concave mirror. The dark field stop is preferably a little larger than the image of the entry diaphragm on the specularly reflecting surface of the mirror wheel.

In a particularly preferred embodiment the light receiving surfaces are provided closely adjacent one another distributed over the entire periphery of the dark field stop. This arrangement makes it possible to detect light deflections in all directions.

As a discrimination between different azimuths of the light deflection is frequently not necessary the light receiving surfaces are expediently connected together groupwise. As a consequence of different undesired scattering effects within the overall arrangement, and also as a consequence of certain normal scattering effects at the material web, as a result of its basic structure, a type of corona frequently arises around the dark field stop, even with faultfree material. This corona could cause the photoreceiver arrangement connected to the light receiving surfaces to respond unnecessarily. In order to overcome this difficulty respective diametrically oppositely disposed groups of light receiving surfaces are connected together to form pairs of photoelectric signals which are applied to difference amplifiers. This embodiment exploits the recognition that the average scattering in all directions of the periphery of the dark field stop is substantially the same, so that the signals of the photoreceivers illuminated by diametrically oppositely disposed light receiving surfaces mutually cancel one another, when they are connected to a differential amplifier. The influence of the corona which can be compared to a basic noise can thus be completely precluded. As faults normally only produce light deflection in a single direction the corresponding light flashes which occur at the edge of the dark field stop cause the output of the differential amplifier to respond in contrast to the corona noise. The embodiment just described thus increases the contrast of fault signals relative to the normal case.

In a particularly preferred embodiment each of said group extends over a quadrant of the dark field stop.

The individual diametrically disposed groups can fundamentally also be processed by means of quotient forming.

As a result of the measures of the invention a displacement of the centre of the corona, such as frequently occurs with foil pictures, can be detected.

The light receiving surfaces may conveniently be formed by the end faces of thin circular light conductors which are led individually or preferably groupwise to photoreceivers.

This embodiment has the advantage that only a few photoreceivers are necessary because only a single photoreceiver is necessary for a plurality of light receiving surfaces. Although many light conductors or fibres are present only four photoreceivers are required (as can be seen from FIG. 5).

In an alternative embodiment the light receiving surfaces are the rectangular end faces of plate-like light conductors which each take in one side of a rectangular or square dark field stop and each lead to a photoreceiver. This has the advantage that he use of a large number of capillary-like light conductors can be avoided.

It is however also possible for the light receiving surfaces to be constructed as photodiodes (in accordance with FIG. 8), with the photodiodes being arranged around the dark field stop as photoreceivers.

It is particularly advantageous if, apart from the light beams which are still very intense but have only been deflected a little, it is also possible to detect the light which is deflected through larger scattering angles and which is less intense. For this purpose the dark field stop is surrounded radially outside of the light receiving surfaces by a ring-like light entry surface which is connected to a further photoreceiver, in particular to a photomultiplier.

With these embodiments it is possible not only to register small angular deviations caused by the material web but also to detect information about faults with greater scattering of the light at the material web. Thus a differentiated detection of the fault signals is realised depending on the angular deviation of the primary beam produced by the material web.

Figure 2:
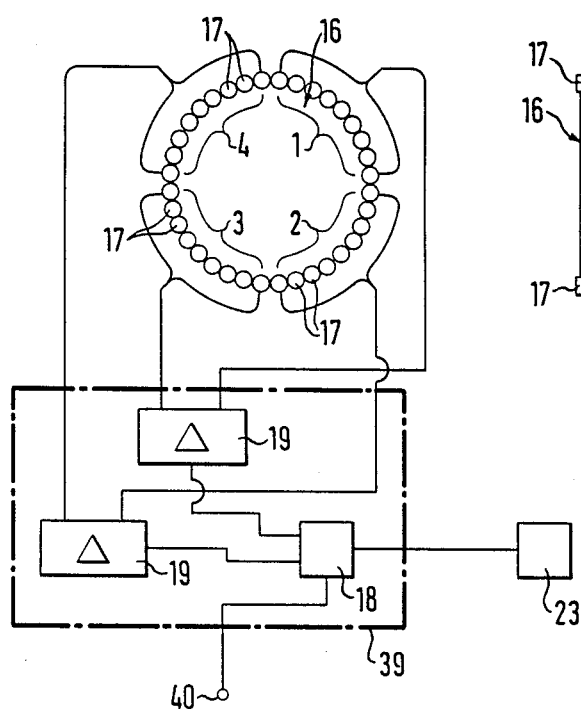
Figure 3:
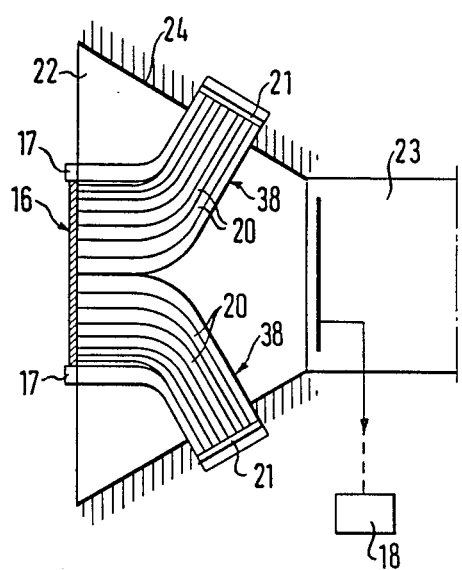
Figure 4:
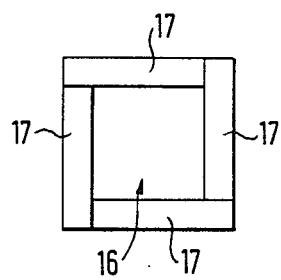
Figure 5:
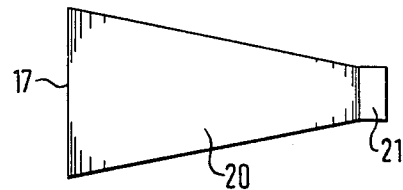
Figure 3A:
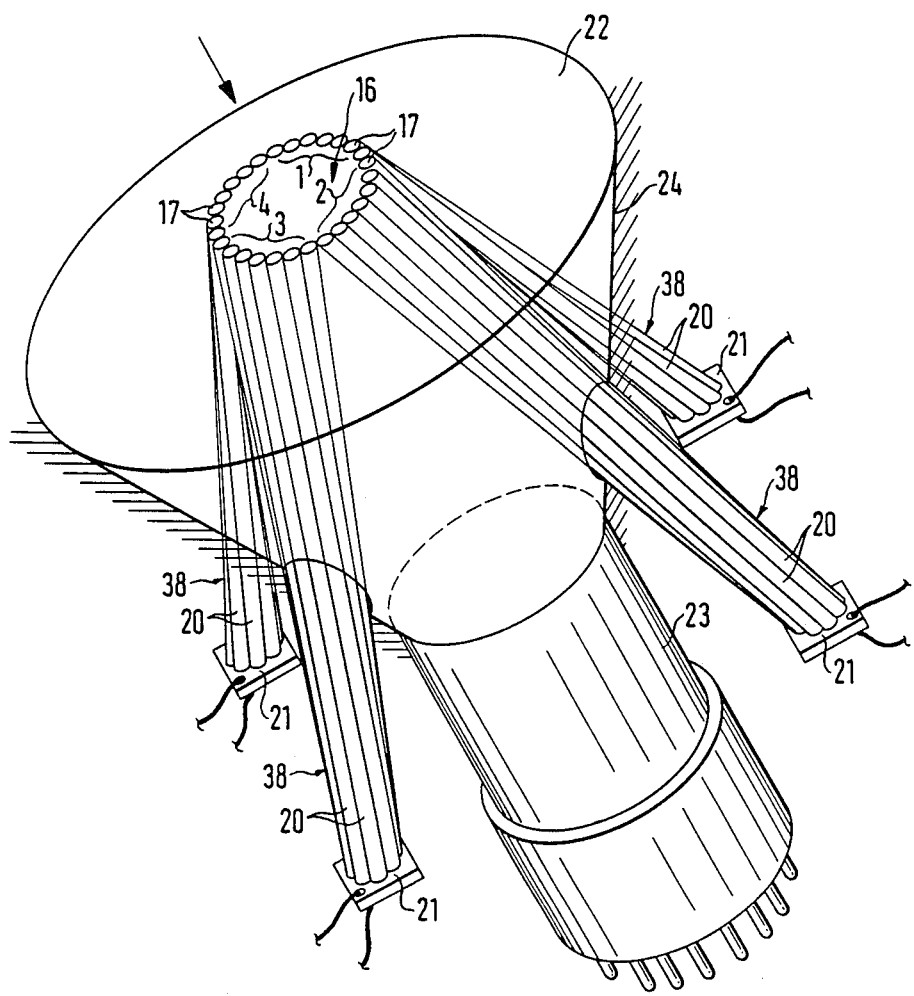
Figure 4A:
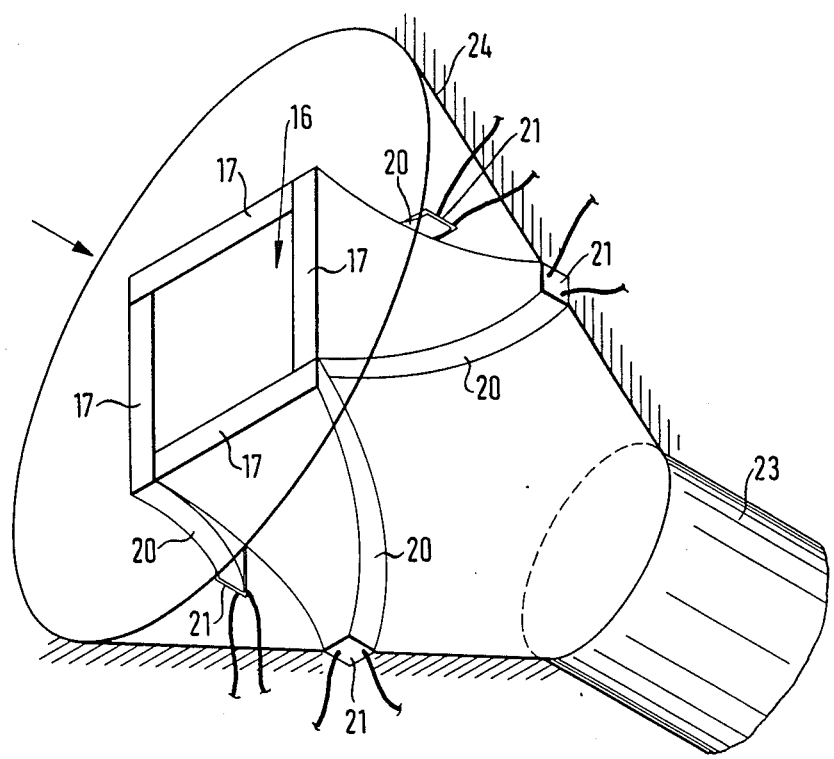

The invention will now be described in the following by way of example with reference to the drawings in which:

FIG. 1 shows a schematic perspective illustration of a web monitoring apparatus in accordance with the invention, FIG. 2 shows a plan view of the dark field stop 16 of FIG. 1 to an enlarged scale with a schematic block representation of the attached electronic circuit, FIGS. 3 and 3a show a side view and a perspective view respectively of the embodiment of FIG. 2 with a photomultiplier also being provided which detects the light which is scattered sideways to a greater degree, FIGS. 4 and 4a show a plan view and perspective view respectively of a further embodiment of a dark field stop in accordance with the invention with light receiving surfaces and a light funnel arranged around it respectively, and FIG. 5 shows a schematic side view of the subject of FIG. 4.

As seen in FIG. 1 a laser 25 sends a sharply bundled convergent light beam via a beam broadening optical system 26 and a plane deflecting mirror 27 onto the mirror surface 11 of a mirror wheel 12 which rotates at high speed in the direction of the arrow f. The mirror surface 11 is arranged spaced by the focal distance from a strip-like concave mirror 15.

An aperture diaphragm 28 is arranged in front of the mirror surface and cuts out a circular region of the beam of light impinging onto the mirror surface 11 so that an exactly circular and sharply bounded light bead exists at the position of this entry pupil 13 of the scanning system. A scanning light beam 30 is directed from the light bead to a plane deflecting mirror 31 and from there onto the strip-like concave mirror 14. On rotation of the mirror wheel in the sense of the arrow f the scanning beam 30 cyclically scans the strip-like concave mirror and sequentially adopts the positions 30' and 30" amongst others.

A scanning beam 32 thus emerges from the strip-like concave mirror 14 which is displaced parallel to itself in the direction of the arrow F. The scanning beam 32 falls onto the surface of a material web 33 and generates a scanning streak or line 34 there as a result of the periodic scanning movement.

The scanning beam 32 is incident on the material web 33 at an angle to the perpendicular. The scanning streak 34 preferably extends transverse to the longitudinal direction L of the web, with the web also being continuously moved in this direction beneath the scanning arrangement.

The beams 35 reflected at the angle of reflection are detected by the receiver side of the concave mirror 15, which is preferably identical to the transmitter side of the concave mirror 14, and are concentrated by the former, via a further strip like plane deflecting mirror 36, and also a deflecting mirror 37, in the focal plane of the concave mirror 14, where an image of the entry pupil 13 is generated on the dark field stop 16. A photomultiplier 23 is arranged behind the dark field stop.

The diameter of the dark field stop 16 is fractionally larger than the diameter of the image of the entry pupil 13. In this manner light normally reflected at the surface of the material web 33 does not reach the photomultiplier 23.

In accordance with the invention the dark field stop 16 is provided, as shown in FIGS. 2, 3 and 3a, all around with a circular arrangement of light receiving surfaces 17 which are formed by the free end faces of light conductors 20. The light conductors 20 are subdivided into quadrants 1, 2, 3 and 4 and are combined quadrant-wise to light conductor bundles 38 which are respectively led to a photoreceiver 21, and are so arranged there that the light picked up by the light conductors 20 at the light receiving surfaces 17 is incident on the associated photoreceiver 21.

The photoreceivers 21 provided for the quadrants 1, 2, 3 and 4 are connected to an electronic processing circuit 39 which contains two difference amplifiers 19. The outputs of the photoreceivers 21 respectively associated with the diametrically oppositely disposed quadrants 1, 3 and 2, 4 respectively are connected to the inputs of the difference amplifiers 19. In this manner it is ensured that no signal arises at the output of the differential amplifiers 19 when the same quantities of light are incident on the light receiving surfaces 17 of diametrically oppositely disposed quadrants. In this way the background noise of the arrangement is eliminated. If, however, only small light deflections occur in one direction, for example through bubbles, streaks or other disturbances at the surface of the material web, then in each case only the photoreceiver 21 associated with one of the quadrants will receive more light, and a signal will arise at the output of the associated difference amplifier 19. This signal will give rise to a fault signal at the output 40 of an electronic processing circuit 18 connected to the two difference amplifiers 19.

As seen in FIGS. 3 and 3a there is provided, around the dark field stop 16 with the light receiving surfaces 17 arranged around it, a ring-like light entry surface 22. A light funnel 24 which tapers away from the dark field stop 16 adjoining the outer periphery of the light entry surface 22 and the photoreceivers 21 are arranged sunk in its walls (FIG. 3). As seen in FIG. 3a the photoreceivers lie behind the light funnel 24. The light conductor bundles 38 are passed either to the recesses (FIG. 3) containing the photoreceivers 21 or through bores in the light funnel 24 to the respective photoreceiver 21 (FIG. 3a).

The light funnel 24 tapers somewhat down to the diameter of the photomultiplier 23 which is secured to the end of the truncated cone-like light funnel 24.

As a result of this arrangement light which is more strongly scattered beyond the light receiving surfaces 17 can pass through the light entry surface 22 to the specularly constructed light funnel 24 from where it is directed/reflected to the photomultiplier 23. The photomultiplier 23 is connected to the electronic processing circuit 18 so that it also causes a corresponding fault signal there on the occurrence of more strongly scattered light rays.

As seen in FIGS. 4 and 4a the dark field stop 16 is of square shape. A square light bead in the entry pupil 13 on the mirror wheel 12 is imaged onto it, in manner not shown, in such a way that the image is somewhat smaller than the dark field stop 16. The rectangular end faces 17 of band-like light conductors indicated in FIG. 5 are arranged around the square dark field stop 16 so that only one light conductor 20 is necessary for each side of the square, with the light conductors contracting conically and possible in curved manner, as shown in FIGS. 4a and 5 and being provided at the end with a photoreceiver 21. FIG. 4a also shows the light funnel 24 which is provided with an internal mirror surface.

The FIGS. 4 and 5 are an example of how the light reception can be realised at the periphery of the dark field stop 16 in different manner. By way of example the light receiving surfaces 17 of FIG. 2 could also be individual photodiodes, or strip-like lenses which each form an image on an associated photodiode.

I claim:

1. Optical web monitoring apparatus which, by means of a deflecting device and image forming optical elements, generates a point of light which cyclically scans the material web transverse to its longitudinal direction and concentrates light deflected or scattered on passage through the material, or on reflection at the material, onto a photoreceiver device, characterized in that a sharply bounded bead of light is generated on the deflecting device (12) which is imaged, through the optical scanning and receiving system (14, 15), onto a complementary dark field stop (16), which is preferably slightly larger than the image of the light bead (13) and which is provided along its periphery with light receiving surfaces (17), which are of small area relative to the extent of the dark field stop (16) and which conduct the received light to the photo-receiver device, which is connected to an electronic processing circuit.

2. Apparatus in accordance with claim 1, characterized in that the light receiving surfaces (17) are provided closely adjacent one another distributed over the entire periphery of the dark field stop (16).

3. Apparatus in accordance with claim 1, characterized in that the light receiving surfaces (17) are connected together to a common photoreceiver (21).

4. Apparatus in accordance with claim 3, characterized in that respective diametrically oppositely disposed groups of light receiving surfaces (17) are connected together to form pairs of photoelectric signals which are applied to difference amplifiers (29).

5. Apparatus in accordance with claim 4, characterized in that each group extends over a quadrant (1, 2, 3, 4) of the dark field stop (16).

6. Apparatus in accordance with claim 1, characterized in that the light receiving surfaces are the end faces of thin circular light conductors (20) which are led individually to photoreceivers (21).

7. Apparatus in accordance with claim 1, characterized in that the light receiving surfaces (17) are the rectangular end faces of light conductors (20) which each take in one side of a rectangular dark field stop (16) and each lead to a photoreceiver (21).

8. Apparatus in accordance with claim 1, characterized in that the dark field stop (16) is surrounded radially outside of the light receiving surfaces by a ring-like light entry surface (22) which is connected to a further photoreceiver, in particular to a photomultiplier (23).

9. Apparatus in accordance with claim 8, characterized in that a reflecting light funnel (24) follows the light entry surface (22) and tapers towards the photoreceiver (23) down to the diameter of the photoreceiver.

10. The apparatus of claim 1 wherein the bead of light has a circular cross-sectional shape.

11. The apparatus of claim 1 wherein the bead of light has a rectangular cross-sectional shape.

12. The apparatus of claim 1 wherein the light receiving surfaces are the end faces of thin circular light conductors (20) which are led to one photoreceiver (21).

13. Optical web monitoring apparatus which, by means of a deflecting device and image forming optical elements, generates a point of light which cyclically scans the material web transverse to its longitudinal direction and concentrates light deflected or scattered on passage through the material, or on reflection at the material, onto a photoreceiver device, characterized in that a sharply bounded bead of light is generated on a correspondingly shaped physical diaphragm (28), which is imaged, through the optical scanning and receiving system (14, 15), onto a complementary dark field stop (16), which is preferably slightly larger than the image of the light bead (13) and which is provided along its periphery with light receiving surfaces (17), which are of small area relative to the extent of the dark field stop (16) and which conduct the received light to the photo-receiver device, which is connected to an electronic processing circuit.

* * * * *